United States Patent [19]

Hines et al.

[11] Patent Number: 4,583,556
[45] Date of Patent: Apr. 22, 1986

[54] MICROWAVE APPLICATOR/RECEIVER APPARATUS

[75] Inventors: Marion E. Hines; Robert J. Bielawa; Robert O. Geoffroy, all of Middlesex County, Mass.

[73] Assignee: M/A-Com, Inc., Burlington, Mass.

[21] Appl. No.: 449,389

[22] Filed: Dec. 13, 1982

[51] Int. Cl.⁴ ............................................. A61N 1/40
[52] U.S. Cl. ................................... 128/804; 128/798; 128/784
[58] Field of Search ............... 128/804, 784, 786, 399, 128/401, 421, 422; 219/10.55 R, 10.55 A, 10.55 M, 10.55 F, 10.81

[56] References Cited

U.S. PATENT DOCUMENTS 4,154,246  5/1979  LeVeen ............................... 128/804

FOREIGN PATENT DOCUMENTS 2027594  2/1980  United Kingdom ................. 128/798

Primary Examiner—Edward M. Coven
Attorney, Agent, or Firm—Wolf, Greenfield & Sacks

[57] ABSTRACT

A microwave applicator for applying microwave energy to living tissue for providing uniform heating without hot spots. The applicator includes a first electrical conductor and a second electrical conductor substantially shielding the first conductor in a transmission line configuration capable of propagating microwave energy in a frequency band suitable for heating living tissue. The first conductor has an unshielded portion extending a distance beyond the second conductor and there is additionally provided a coil as a third electrical conductor surrounding the extending portion of the first conductor and connected between the ends of the first and second conductors. The applicator is preferably configured for insertion through an opening into the body and includes a substantially smooth dielectric sleeve covering the coil of the third conductor.

7 Claims, 4 Drawing Figures

MICROWAVE APPLICATOR/RECEIVER APPARATUS

INTRODUCTION

This invention relates in general to methods and means for hypothermal medical treatment. More particularly the invention discloses an applicator for applying microwave energy to living tissue within a human or animal body for uniformly heating such tissue without "hot spots", and a novel method for achieving such uniform heating, to any desired temperature in a range including temperatures which will destroy tumorous tissue while being safe for viable tissue.

Prior known applicators for this purpose are in the configuration of a simple coaxial monopole (illustrated at FIG. 2(a) of the accompanying drawings), which is characterized by intense heating in a region where the inner and outer conductors are close together; FIG. 2(a) illustrates the isothermal field lines of that kind of applicator.

The following prior art is noted:
Kraus "ANTENNAS", McGraw-Hill 1950, chapter 7, Sec. 7-16, pages 213-215; U.S. Pat. No. 3,014,791—Dec. 26, 1961—Benzing, et al.

SUMMARY OF THE INVENTION

Accordingly, it is an object of the invention to provide an applicator sufficiently small, especially sufficiently thin, so that it may be inserted into the body for hypothermal medical treatment purposes. Such purposes include measurement of local temperature differences by radiometry, and heating of living tissue by application of RF energy.

Another object of the present invention is to provide an applicator which heats the active zone of tissue uniformly, avoiding the creation of "hot spots" which could burn tissue and cause pain.

In accordance with the present invention, an applicator is made of a first electrical conductor and a second electrical conductor substantially shielding said first conductor in a transmission line configuration capable of propagating microwave energy in a frequency band suitable for heating living tissue; the first conductor has an unshielded portion extending a distance beyond said second conductor; and a coil of a third electrical conductor surrounding the extending portion of the first conductor is connected between the ends of the first and second conductors. This arrangement is capable of providing a pattern of microwave radiation into living tissue which pattern is characterized by substantially uniform non-burning intensity distribution over a prescribed spatial distribution within said tissue. The applicator is configured for insertion through an opening into said body, and it includes a substantially smooth dielectric sleeve covering the coil of the third conductor.

BRIEF DESCRIPTION OF THE DRAWINGS

Numerous other objects, features and advantages of the invention should now become apparent upon a reading of the following detailed description taken in conjunction with the accompanying drawing, in which.

DETAILED DESCRIPTION

Figure 1:
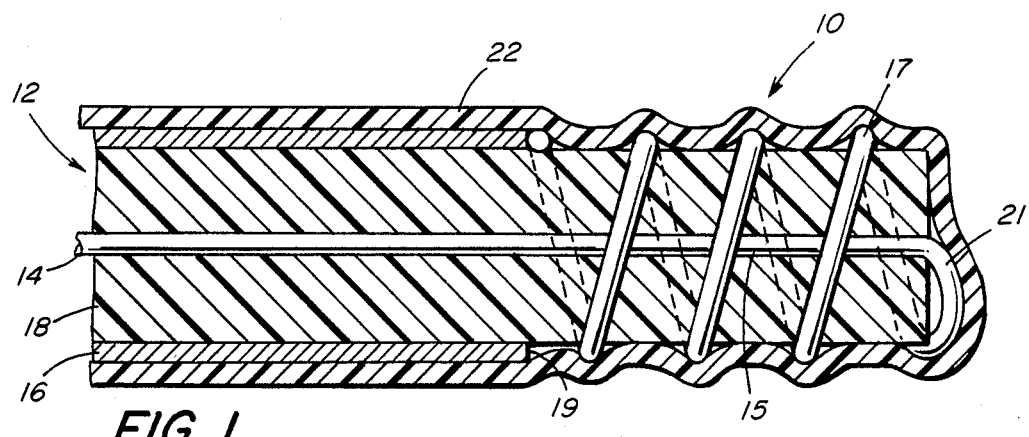
FIG. 1 is a side-sectional view of an applicator according to the invention.

The applicator shown in FIG. 1 is the heating tip 10 of a unit intended to be inserted into a body cavity or duct for heating living tissue within the body with radio-frequency energy in a microwave frequency band, fixed to an end of a coaxial line 12. The coaxial line comprises the usual center conductor 14, outer conductor 16 and dielectric 18 between them. This is the RF input to the heating tip 10. The outer conductor 16 is removed to expose an end portion 15 of the inner conductor 14. A coil of a third conductor 17 surrounds the end portion 15 and dielectric 18 which envelopes it; the third conductor is, by conductive connection, connected in series between the end 19 of the outer conductor and the end 21 (radial conductor) of the end portion 15. A smooth insulating dielectric sleeve 22 surrounds the heating tip 10 and the immediately—adjacent portion of the outer conductor 16.

Figure 2A:
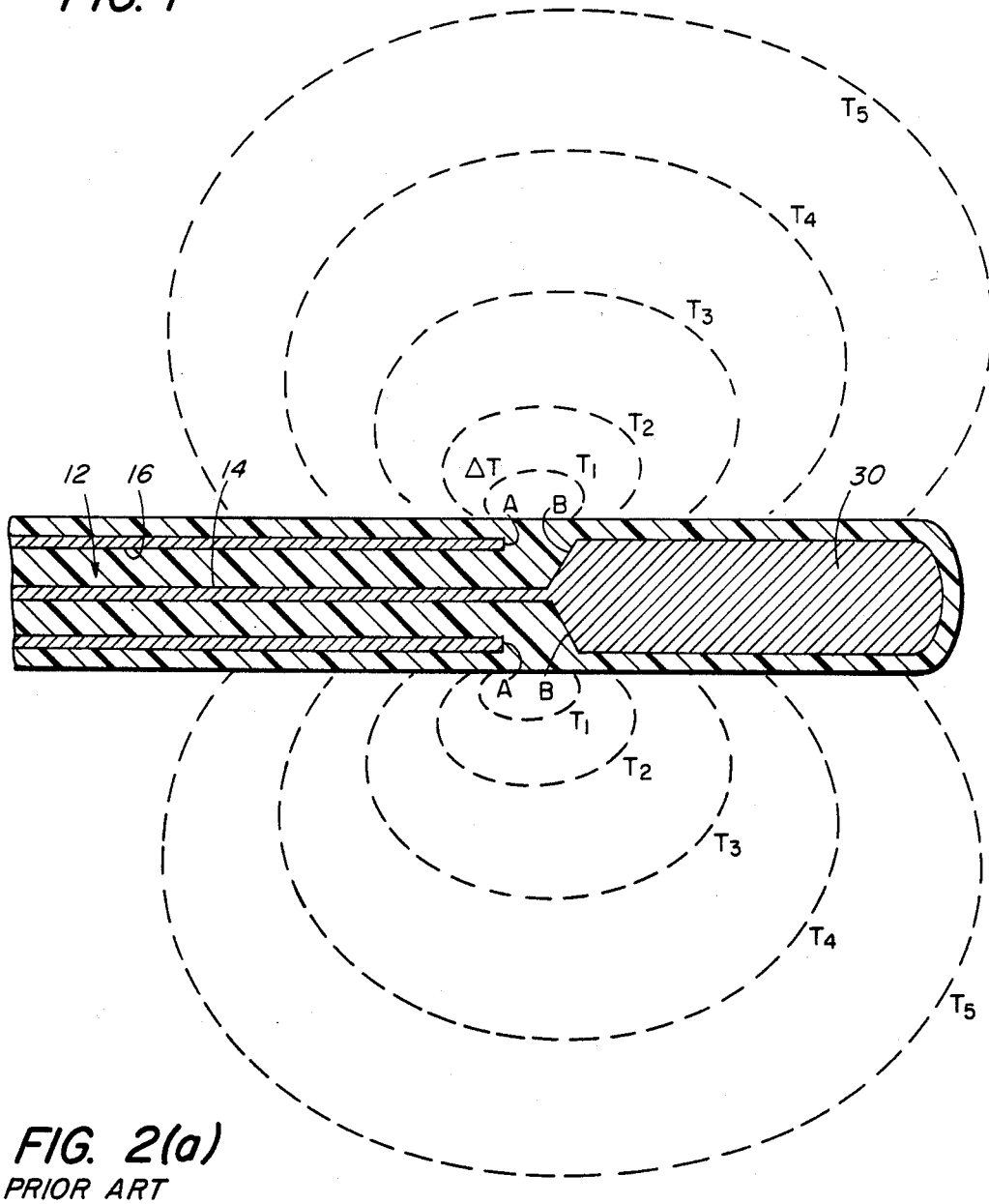
FIGS. 2(a) and (b) are sketches showing isothermal lines in the radiation fields of the prior-known coaxial monopole applicator referred to above and the applictor of FIG. 1, respectively.
Figure 2B:
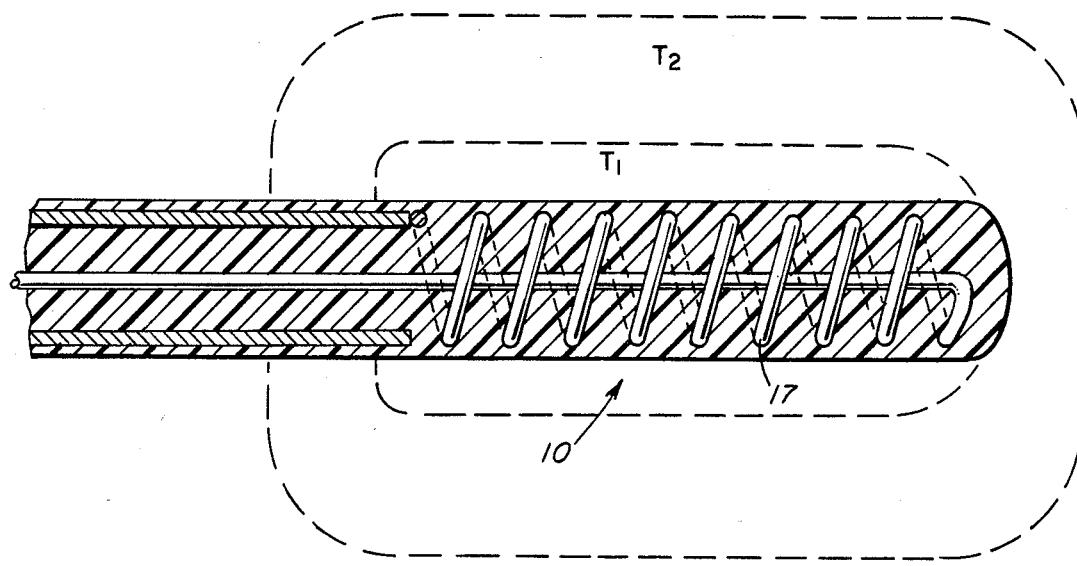

When the applicator of FIG. 1 is inserted into living tissue and microwave-frequency energy is applied to the coaxial line 12, local RF heating of the surrounding tissue will occur, the temperature reached in the tissue depending on many known factors such as power, inverse-square law radiation decrements, etc. FIGS. 2(a) and (b) respectively illustrate the approximate field pattern of a prior art applicator as compared with an applicator constructed in accordance with the present invention. In FIG. 2(b) reference characters similar to those in FIG. 1 are used; in FIG. 2(a) the coaxial line section 12 is coupled at the center conductor 14 to a monopole 30, which is free of the outer conductor 16. A high-voltage gradient exists between the monopole 30 and the outer conductor 16 where they are closest together; i.e.: between a circular locus A at the end of the outer conductor 16 and a circular locus B on the monopole 30 which is nearest to it. The radiation field is strongest between these two loci, and tapers off in strength between regions of the outer conductor 16 and monopole 30 which are progressively further apart. Thus, the isothermal lines T1, T2—Tn, shown in FIG. 2(a) show that the temperature achieved in tissue in contact with the applicator varies along the applicator, with the potential for an excessively hot ring in the annular region between locus A and locus B. This puts a limit on how much power can be applied to the RF input for heating tissue more remote from the applicator.

Referring to FIG. 2(b), the isothermal lines T1 and T2 indicate that heating of tissue surrounding the applicator is more nearly uniform along the applicator. The coil 17 is electrically connected at its ends to the inner and outer conductors, respectively, and there is no region axially along the heating tip 10 where the RF field is substantially stronger than in any other region. Thus the isothermal line T1 representing the highest temperature nearest to the applicator, is nearly flat throughout the axial extent of the heating tip. Direct electrical connections at the ends of the third conductor 17 eliminate any field build-up at the heating tip. Thus, with an applicator of the invention, RF power can be increased without causing a hot spot, or a hot ring. The power can be raised substantially entirely in accordance with what temperature the user desires to achieve in surrounding tissue for hypothermal medical purposes. Alternatively, an applicator according to the invention is a superior detector of heat being radiated from within the surrounding tissue, in that the predictably uniform radiation field indicated in FIG. 2(b) enables more reliable location of a source of heat within the tissue.

In brief, applicators according to the invention can provide a more uniform heating or detection measurement of temperature over a wider zone of the human body than has heretofore been possible. Such improved capability is thought to be useful for detection and possible heat treatment of cancer sites within living tissue.

Figure 3:
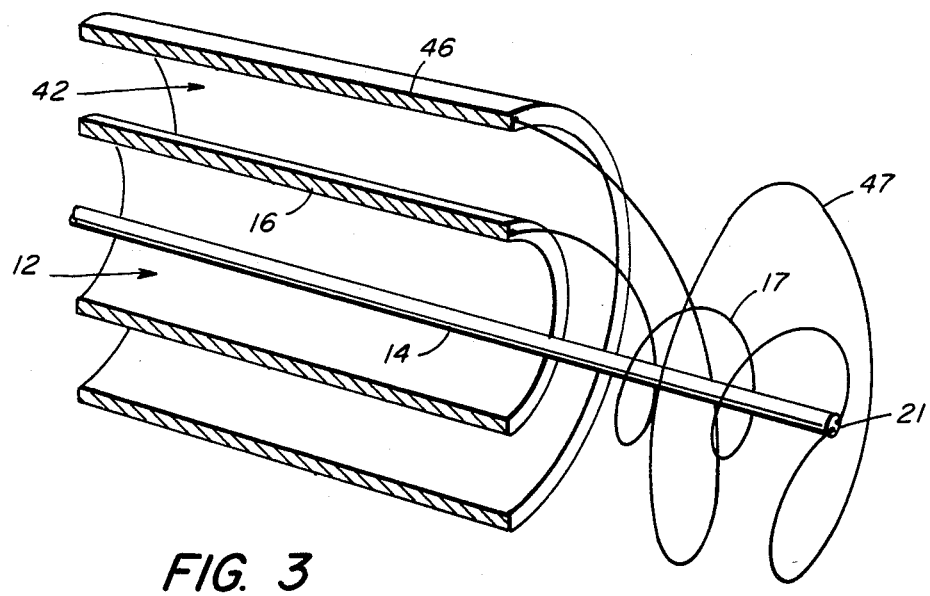
FIG. 3 is a side-sectional view, partly schematic, of a two-frequency applicator according to the invention.

In FIG. 3 the first coaxial line section 12 of FIG. 1 is surrounded by a second coaxial line section 42, the outer conductor 16 of the first section 12 being the inner conductor of the second section 42. The conductor 46 of the second section is a fourth conductor of the assembly. A second coil of a fifth conductor 47 surrounds the first coil of the third conductor 17, the fifth conductor being connected between the first conductor 14 and the fourth conductor 46. This is a dual-frequency applicator/probe, the second coil of conductor 47 and outer coaxial line section 42 being intended for use at a lower frequency than the first coil of conductor 17 and inner coaxial line section 12. The coils are similarly connected between the free end 21 of the first inner conductor 14 and the ends of the respective outer conductors 16 and 46.

The coils of conductors 17 and 47 may be helical, in which event FIG. 3 includes the case of two concentric helices.

We claim:

1. For use in medical treatment of living tissue a microwave applicator/receiver device capable of applying microwave-frequency radiant energy to living tissue by way of insertion thereof through an opening into the body and of receiving similar energy radiating from within such tissue while in contact with said tissue, said device comprising an inner electrical conductor and an outer electrical conductor substantially shielding said inner conductor in a non-resonant transmission line configuration capable of propagating microwave energy in a frequency band suitable for heating living tissue, said inner conductor having an unshielded portion extending a distance beyond said outer conductor, and a helical coil surrounding said extending portion of said inner conductor and including first and second means connected between the ends of said outer and inner conductors respectively, for providing a traveling wave pattern of microwave radiation into tissue which pattern is characterized by substantially uniform intensity distribution over a prescribed spatial distribution within said tissue thus providing uniform heating absent hot-spots over the length of said helical coil, said first means providing a conductive connection from the outer conductor to the helical coil, said second means comprising a substantially radial conductor interconnecting the helical coil with the inner conductor extending portion with an absence of any conductor extending axially substantially beyond said helical coil, said helical coil having multiple wire turns each separated from the next by an inter-turn spacing greater than the diameter of the helical conductor wire, the axial length of said helical coil being substantially greater than the diameter of the helical coil, and including a substantially smooth dielectric sleeve covering at least said helical coil.

2. A device according to claim 1 in which said outer conductor substantially coaxially surrounds said inner conductor.

3. A device according to claim 2 wherein said substantially smooth dielectric sleeve covers both said helical coil and an immediately-adjacent portion of said outer conductor.

4. A device according to claim 2 including a third conductor surrounding and spaced from said outer conductor, and a second coil of a fourth electrical conductor surrounding and spaced from said helical coil and connected between the ends of said inner and third conductors, for propagating microwave energy in a second frequency band removed from said first-named frequency band.

5. A device according to claim 1 in which the outer conductor substantially, coaxially surrounds said inner conductor with said first means providing a direct substantially point conductor contact between the coaxial outer conductor and helical coil.

6. A device according to claim 1 wherein said radial conductor is slightly curved to provide a smooth conductive transition from the inner conductor to the helical coil.

7. A device according to claim 1 wherein the helical coil comprises a helix wire having a length substantially greater than a minor fraction of one quarter wavelength at the operating frequency band.

* * * * *